United States Patent
Tsukada et al.

(10) Patent No.: US 9,140,636 B2
(45) Date of Patent: Sep. 22, 2015

(54) BRIQUETTE INSPECTION DEVICE AND BRIQUETTE INSPECTION METHOD FOR MEASURING WEIGHT, VOLUME, AND CRUSH STRENGTH

(71) Applicants: Furukawa Co., Ltd., Tokyo (JP); Furukawa Industrial Machinery Systems Co., Ltd., Tokyo (JP)

(72) Inventors: Koji Tsukada, Tochigi (JP); Fumio Yuasa, Ibaraki (JP)

(73) Assignees: Furukawa Co., Ltd., Tokyo (JP); Furukawa Industrial Machinery Systems Co., Ltd., Tokyo (JP)

( * ) Notice: Subject to any disclaimer, the term of this patent is extended or adjusted under 35 U.S.C. 154(b) by 52 days.

(21) Appl. No.: 14/088,486

(22) Filed: Nov. 25, 2013

(65) Prior Publication Data

US 2014/0146310 A1 May 29, 2014

(30) Foreign Application Priority Data

Nov. 27, 2012 (JP) .................................. 2012-258587

(51) Int. Cl.
| | |
|---|---|
| *G01N 21/84* | (2006.01) |
| *G01N 3/00* | (2006.01) |
| *G01B 11/00* | (2006.01) |
| *G01N 3/08* | (2006.01) |
| *G01B 11/04* | (2006.01) |

(52) U.S. Cl.
CPC *G01N 3/00* (2013.01); *G01B 11/00* (2013.01); *G01N 3/08* (2013.01); *G01B 11/04* (2013.01); *G01N 2203/0076* (2013.01); *G01N 2203/0087* (2013.01)

(58) Field of Classification Search
CPC .... B30B 11/006; B30B 11/16; B30B 15/308; G01B 11/02; G01B 11/00; G01B 11/022; G01B 11/024; G01B 11/04; G01B 11/043; G01B 11/046; G01N 2021/845; G01N 2203/0087; G01N 2203/0076
USPC .................... 425/145, 149, 79, 150, 237, 363
See application file for complete search history.

(56) References Cited

U.S. PATENT DOCUMENTS

| | | | | |
|---|---|---|---|---|
| 4,413,967 A | * | 11/1983 | Burry | 425/149 |
| 6,680,070 B1 | * | 1/2004 | Howarth et al. | 424/484 |
| 2008/0197054 A1 | * | 8/2008 | Lindstrom | 209/517 |
| 2009/0119981 A1 | * | 5/2009 | Drozd et al. | 44/544 |
| 2009/0214724 A1 | * | 8/2009 | Gordon et al. | 426/129 |

FOREIGN PATENT DOCUMENTS

| | | |
|---|---|---|
| JP | 09-174294 A | 7/1997 |
| JP | 09-192896 A | 7/1997 |

* cited by examiner

*Primary Examiner* — Tarifur Chowdhury
*Assistant Examiner* — Michael P. LaPage
(74) *Attorney, Agent, or Firm* — Hammer & Associates, P.C.

(57) ABSTRACT

A briquette inspection device and a briquette inspection method are capable of measuring at least a volume and a crush strength of an identical briquette sample. The briquette inspection device 10 is provided with: a volume measuring unit 2 for measuring the volume of the briquette sample B by laser scanning; and a crush strength measuring unit 3 for measuring the crush strength of the briquette sample B by pressing down and crushing the briquette sample B after the volume measuring unit measures the volume of the briquette sample.

8 Claims, 3 Drawing Sheets

BRIQUETTE INSPECTION DEVICE AND BRIQUETTE INSPECTION METHOD FOR MEASURING WEIGHT, VOLUME, AND CRUSH STRENGTH

TECHNICAL FIELD

The present invention relates to a briquette inspection device for measuring physical properties (apparent density, crush strength, and the like) of granulated substances (briquettes) produced by a granulator (briquetting machine), and a briquette inspection method.

BACKGROUND ART

The briquetting machine produces the briquettes by successively supplying the materials or the raw materials between a pair of rotating rolls and applying a high-compressive force to the supplied materials (see Patent Documents 1 and 2, for example).

The quality control in the production process of the briquettes produced by the briquetting machine can be done by an operator regularly sampling a part of the produced briquettes and determining the state of the sampled briquette (i.e., briquette sample) as a numerical value in consideration of the physical properties such as the apparent density, the crush strength, and the like. It is noted that the apparent density can be calculated by volume and weight of a briquette.

Conventionally, as a method of measuring the volume of the briquette, the briquette taken as a sample is immersed in a liquid of paraffin or the like (without briquette solubility) in a container such as a measuring cylinder, and an increase in its liquid level is measured.

PRIOR ART DOCUMENTS

Patent Documents

Patent Document 1: JP H09-174294 A
Patent Document 2: JP H09-192896 A

SUMMARY OF THE INVENTION

Problem to be Solved

In the conventional volume measuring method, however, the briquette sample is immersed in the liquid of paraffin or the like, the liquid permeates the surface of the sample and its strength decreases. For this reason, it is difficult to measure the crush strength of the identical sample with accuracy.

Therefore, the present invention has been made in view of the above problem and an object of the present invention is to provide a briquette inspection device capable of measuring at least the volume and the crush strength of an identical briquette sample, and an inspection method of the briquette.

Solution to the Problem

In order to solve the above problem, according to an aspect of the present invention, there is provided a briquette inspection device that measures at least a volume and a crush strength of a briquette sample, the briquette inspection device comprising: a volume measuring unit for measuring the volume of the briquette sample by laser scanning; and a crush strength measuring unit for measuring the crush strength of the briquette sample by pressing the briquette sample after the volume measuring unit measures the volume of the briquette sample.

Herein, preferably, the above-described briquette inspection device further comprises: a weight measuring unit for measuring a weight of the briquette sample; and a data processing unit for processing data of the volume measured by the volume measuring unit and data of the weight measured by the weight measuring unit, wherein the data processing unit calculates an apparent density of the briquette sample from the volume measured by the volume measuring unit and the weight measured by the weight measuring unit.

In addition, preferably, in the above-described briquette inspection device, the volume measuring unit measures a cross-sectional shape of the briquette sample by a pair of upper and lower laser measuring devices carrying out laser scanning from above and below on the briquette sample, and the data processing unit distinguishes a front and a back of the briquette sample based upon data of the cross-sectional shape measured by the volume measuring unit.

Furthermore, preferably, the above-described briquette inspection device further comprises an image processing unit for picking up an image of the briquette sample before the volume measuring unit measures the volume of the briquette sample and the crush strength measuring unit measures the crush strength of the briquette sample, wherein the data processing unit checks data of the image of the briquette sample picked up by the image processing unit with a predefined template, and when a difference in an area between the data of the image and the predefined template exceeds a preset range of the area, determines the briquette sample to be inappropriate for a measurement target and excludes the briquette sample from the measurement target at the volume measuring unit and at the crush strength measuring unit.

Further, preferably, in the above-described briquette inspection device, the volume measuring unit measures an outer shape of the briquette sample by the laser scanning, and the data processing unit checks data of the outer shape of the briquette sample measured by the volume measuring unit with a predefined template, and when a difference in an area between the data of the outer shape and the predefined template exceeds a preset range of the area, determines the briquette sample to be inappropriate for a measurement target and excludes the briquette sample from the measurement target based upon the cross-sectional shape at the volume measuring unit and at the crush strength measuring unit.

Moreover, in order to solve the above problem, according to another aspect of the present invention, there is provided a briquette inspection method for measuring at least a volume and a crush strength of a briquette sample, the briquette inspection method comprising: measuring the volume of the briquette sample by laser scanning; and measuring the crush strength of the briquette sample by pressing the briquette sample after the measuring step measures the volume of the briquette sample.

Advantageous Effects of the Invention

According to the present invention, the volume of the briquette sample is measured by laser scanning, thereby eliminating the necessity of immersing the briquette sample into the liquid of paraffin or the like. Therefore, after the volume is measured, the crush strength of the identical briquette sample the volume of which has been measured can be measured with accuracy.

DESCRIPTION OF EMBODIMENTS

Figure 1:
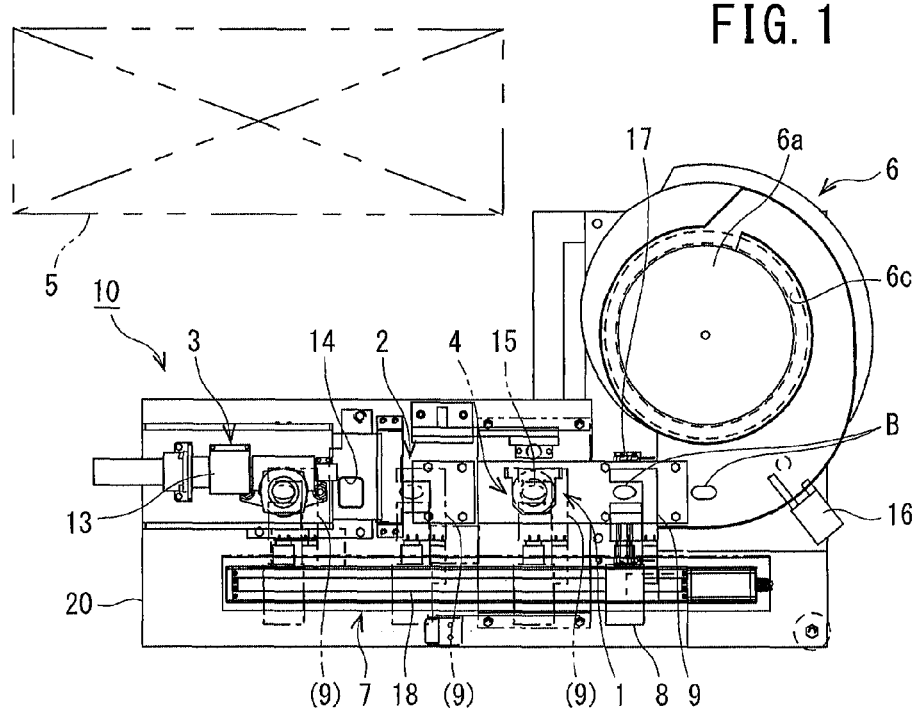
FIG. 1 is a plain view illustrative of a briquette inspection device according to an embodiment of the present invention.
Figure 2:
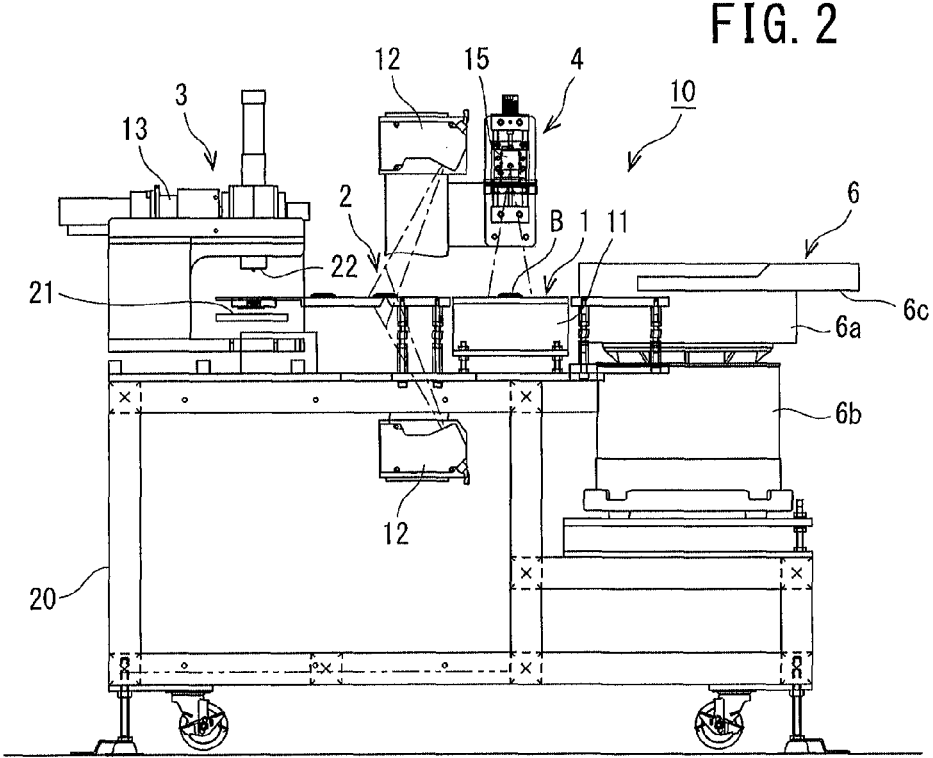
FIG. 2 is a front view of the briquette inspection device of FIG. 1.
Figure 3:
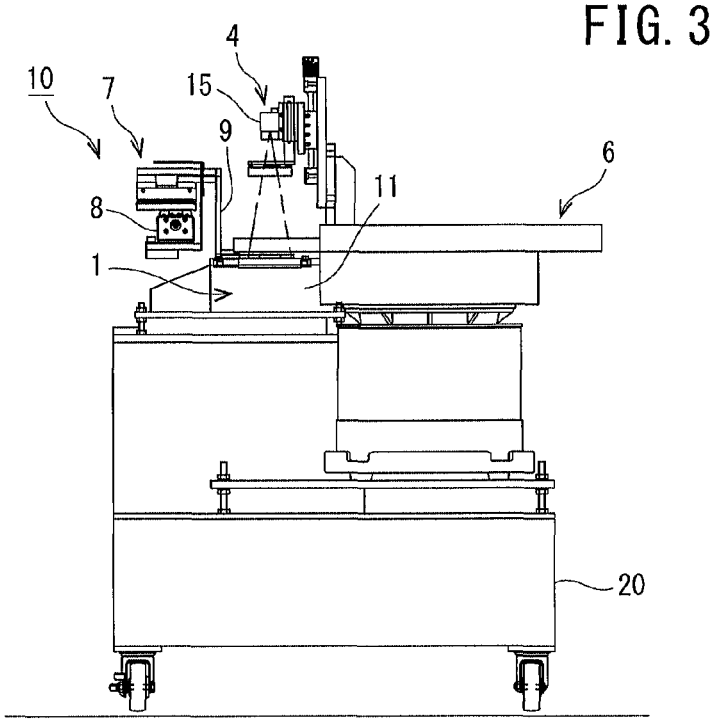
FIG. 3 is a right-side view of the briquette inspection device of FIG. 2.
Figure 4:
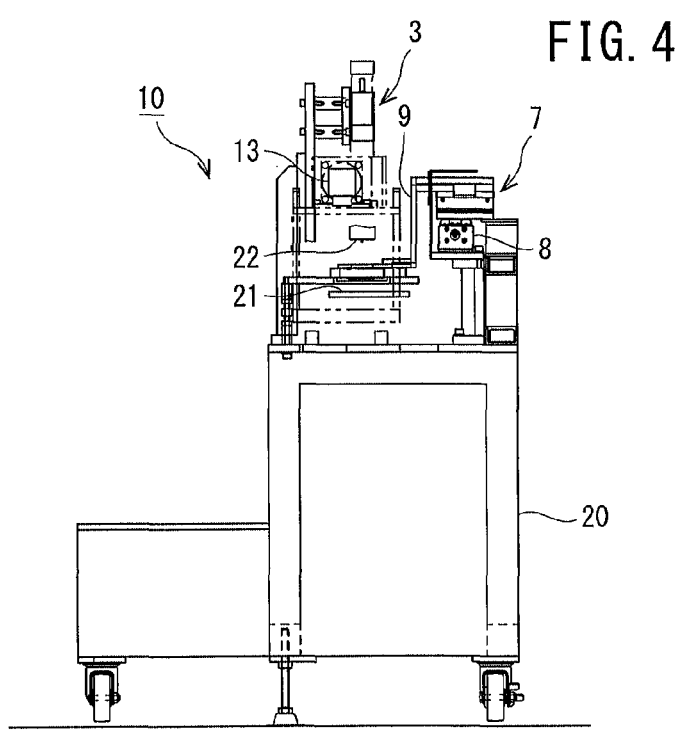
FIG. 4 is a left-side view of the briquette inspection device of FIG. 2.

Hereinafter, an embodiment of the present invention will be described with reference to the drawings.

Referring to FIG. 1 to FIG. 4, a briquette inspection device 10 has a housing 20 made of steel, and a conveyance feeder 6 is mounted and secured on one end of the housing 20.
The conveyance feeder 6 includes: a bowl 6a having a projection on its center; a vibrating unit 6b below the bowl 6a; a conveyance path 6c formed in a spiral shape along the wall surface of the bowl 6a; and an opening and closing device 16 arranged in the partway of the conveyance path 6c. In addition, the outlet of the conveyance path 6c is provided with a detection sensor 17 for detecting a briquette sample B.

The conveyance feeder 6 is arranged such that the briquette sample B selected at random from the upstream process side drops onto the bowl 6a. The briquette samples B in the bowl 6a are aligned along the conveyance path 6c by the vibration of the vibrating unit 6b, and are conveyed to the downstream side. The opening and closing device 16 is configured to block the conveyance path 6c when one briquette sample B is conveyed to the detection sensor 17, so that the subsequent briquette samples B will not move to the position of the detection sensor 17.

On the downstream side of the conveyance feeder 6, as illustrated in FIG. 1, a linear guide device 7 is provided on the housing 20 in the left-right direction of FIG. 1. The linear guide device 7 has a slide mechanism 8. The slide mechanism 8 is provided with a holder 9 capable of holding the briquette sample B. The slide mechanism 8 has a ball screw unit and a drive unit, which are not illustrated. The holder 9 is configured to slideably move along a guide rail 18 by the feeding action of the ball screw unit when the drive unit is driven. The holder 9 is configured to stop at the initial position to oppose the detection sensor 17. When the detection sensor 17 detects that one briquette sample B is conveyed, the holder 9 is capable of moving along the guide rail 18 while holding the afore-mentioned briquette sample B.

In this situation, in the briquette inspection device 10, in the slide movement direction of the holder 9 in the linear guide device 7, a weight measuring unit 1, a volume measuring unit 2, and a crush strength measuring unit 3 are arranged in this order from the upstream side in the conveyance direction. Then, the activation of the slide mechanism 8 causes the holder 9 to stop at respective positions corresponding to the weight measuring unit 1, the volume measuring unit 2, and the crush strength measuring unit 3.

The weight measuring unit 1 has a load cell 11, and is capable of measuring the weight of the briquette sample B mounted on the load cell 11. A pair of laser measuring devices 12 are arranged on the upper and lower sides of the volume measuring unit 2, and the laser measuring devices 12 is capable of optically measuring the cross-sectional shape of the briquette sample B by laser scanning the briquette sample B from above and below.

Further, the crush strength measuring unit 3 is provided with a load cell 21 and a pressing mechanism 13. The pressing mechanism 13 has a pressing unit 22 arranged above the load cell 21. The pressing unit 22 is made to go up and down by the activation of the pressing mechanism 13, and is capable of pressing the briquette sample B on the load cell 21. The crush strength measuring unit 3 presses the briquette sample B between the pressing unit 22 and the load cell 21 according to the activation of the pressing mechanism 13, and measures at the load cell 21 the load applied when the briquette sample B is broken by the pressing, as the crush strength. It is to be noted that a disposal outlet 14 for disposing of unnecessary briquette samples B is provided at a position between the volume measuring unit 2 and the crush strength measuring unit 3.

Furthermore, an image processing unit 4 is arranged above the weight measuring unit 1. The image processing unit 4 has a camera 15, and the camera 15 is capable of picking up images of the briquette samples B. Moreover, a data processing unit 5 including a personal computer is arranged in the vicinity of the housing 20, so that the data obtained by the measuring units of the weight measuring unit 1, the volume measuring unit 2, the crush strength measuring unit 3, the image processing unit 4, or the like are output to the data processing unit 5.

Next, the operation (inspection method) of the briquette inspection device 10 will be described.

As to the briquette samples B loaded onto the conveyance feeder 6 of the briquette inspection device 10, one briquette sample B is taken out in cooperation of the detection sensor 17 and the opening and closing device 16. The afore-mentioned one briquette sample B is held by the holder 9, and is firstly carried to the position of the image processing unit 4 by the slide movement of the holder 9.

The image processing unit 4 picks up an image of the briquette sample B with the camera 15. The image data of the briquette sample B obtained by picking up the image is output to the data processing unit 5. The data processing unit 5 processes the image data to calculate a project area of the briquette sample B. The data processing unit 5 checks the image data of the briquette sample B with a predefined template, and calculates a difference in the area between the project area of the briquette sample B calculated from the image data and the project area of the template. Then, when the difference in the area exceeds a preset range of the area (for example, when too big or too small), the data processing unit 5 determines that the briquette sample is inappropriate for a measurement target, and the briquette sample is excluded from the measurement target at the weight measuring unit 1, the volume measuring unit 2, and the crush strength measuring unit 3. The briquette sample B excluded from the measurement target is conveyed to the disposal outlet 14 by the slide movement of the holder 9. When it is positioned above the disposal outlet 14, the holder 9 releases holding of the briquette sample B and thereby disposes of the briquette sample B that has been determined to be inappropriate for the measurement target.

The briquette sample B that has been determined to be appropriate for the measurement target is to be measured at each measuring unit of the weight measuring unit 1, the volume measuring unit 2, and the crush strength measuring unit 3. Specifically, the briquette sample B is mounted on the load cell 11 in the weight measuring unit 1 provided below the image processing unit 4 and its weight is measured. It is to be noted that the weight of the briquette sample B may be measured at the same time with the image processing unit 4 picking up the image, or may be measured before the image processing unit 4 picks up the image. The result of the weight measurement is output to the data processing unit 5.

Subsequently, the briquette sample B that has passed through the image processing unit 4 is carried to the volume measuring unit 2 by the slide movement of the holder 9. In the volume measuring unit 2, the pair of upper and lower laser measuring devices 12 measure the cross-sectional shape (cross-sectional area data and cross-sectional shape data) of the briquette sample B by laser scanning vertically. The measured cross-sectional shape data is output to the data processing unit 5. The data processing unit 5 calculates the volume of the briquette sample B from the obtained cross-sectional area data. Additionally, the data processing unit 5 calculates the apparent density of the briquette sample B from the calculated volume data and weight data. Next, the briquette sample B with its volume calculated is carried to the crush strength measuring unit 3 by the slide movement of the holder 9. The crush strength measuring unit 3 crushes the briquette sample B by pressing it down to measure its crush strength. The measurement result of the crush strength is output to the data processing unit 5.

The data processing unit 5 outputs to an output device, not illustrated, physical properties including the weight, volume, crush strength, and apparent density of one briquette sample B that is the measurement target, from each of the measurement data obtained by the weight measuring unit 1, the volume measuring unit 2, the crush strength measuring unit 3, and the image processing unit 4. This permits an operator to understand the state of one briquette sample B that is the measurement target from the physical properties output as numerical values. It is thus possible to carry out the quality control with sufficient objectivity and high accuracy.

Next, operation effects of the above-described briquette inspection device 10 and the inspection method by use of the briquette inspection device 10 will be described.

The briquette inspection device 10 includes: the volume measuring unit 2 for measuring the volume of the briquette sample B by the laser scanning; and the crush strength measuring unit 3 for measuring the crush strength of the briquette sample B by pressing down the briquette sample B after the volume measuring unit 2 measures its volume. Since the volume of the briquette sample B is obtained by the laser scanning, the sample need not be immersed in a liquid of paraffin or the like. Accordingly, it is possible to measure the volume and the crush strength with accuracy based upon the identical sample carried to the crush strength measuring unit 3, after its volume is measured by the volume measuring unit 2.

In addition, according to the briquette inspection device 10, the briquette inspection device 10 includes: the weight measuring unit 1 for measuring the weight of the briquette sample B; and the data processing unit 5 for processing the measurement data measured by the weight measuring unit 1 and the volume measuring unit 2. Since the data processing unit 5 calculates the apparent density from the weight measured by the weight measuring unit 1 and the volume measured by the volume measuring unit 2, the data processing unit 5 is suited for measuring the physical properties (i.e., apparent density and crush strength) of the briquette to be produced, and is capable of carrying out better quality control.

Furthermore, according to the briquette inspection device 10, the image processing unit 4 for picking up images of the briquette samples B is further provided in the process prior to the measurements at the volume measuring unit 2 and the crush strength measuring unit 3. The data processing unit 5 checks the image data of the briquette sample B obtained by the image processing unit 4 with the predefined template. When the difference in the project area between the image data and the template exceeds a preset range of the area, the corresponding briquette sample is determined to be inappropriate for the measurement target and is excluded from the measurement target at the volume measuring unit 2 and the crush strength measuring unit 3. Therefore, it is preferable to carry out the quality control in accordance with predefined specifications in an efficient manner, based upon the predefined template.

It is to be noted that the briquette inspection device and briquette inspection method are not limited to the above embodiment. Various modifications may occur without departing from the scope of the present invention.

For example, in the above-described embodiment, the pair of upper and lower laser measuring devices 12 carries out the laser scanning from above and below on the briquette sample B. In this situation, the volume measuring unit 2 can cause the pair of upper and lower laser measuring devices 12 to carry out the laser scanning from above and below on the briquette sample B, and in addition, to measure the cross-sectional shape thereof. The data processing unit 5 can distinguish the front and back of the briquette sample B based upon the data of the cross-sectional shape data obtained by each of the laser measuring devices 12.

Figure 5A:
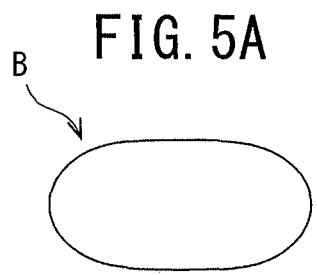
FIG. 5A is a plan view of a first example of a briquette sample.
Figure 5B:
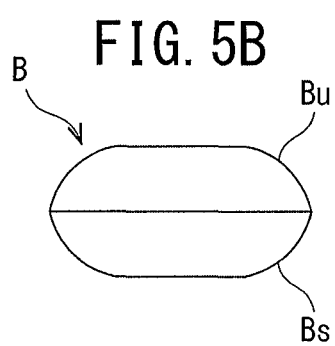
FIG. 5B is a front view of the first example of the briquette sample.
Figure 5C:
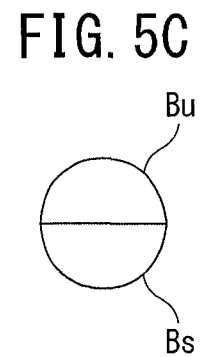
FIG. 5C is a side view of the first example of the briquette sample.
Figure 6A:
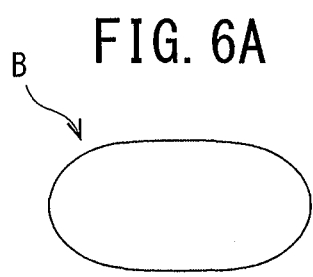
FIG. 6A is a plan view of a second example of the briquette sample.
Figure 6B:
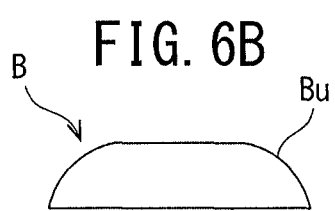
FIG. 6B is a front view of the second example of the briquette sample.
Figure 6C:
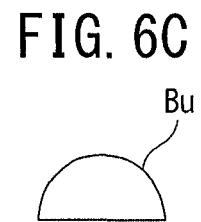
FIG. 6C is a side view of the second example of the briquette sample.

That is, as described above, the briquetting machine is configured such that briquettes as granulated substances are produced by successively supplying materials or raw materials between a pair of rotating rolls and applying a high-compressive force to the supplied materials. When forming portions (concave portions) provided on the pair of rolls have the same shapes, respectively, the briquette sample B includes an upper side Bu and a lower side Bs that are symmetric, as illustrated in FIG. 5A to FIG. 5C, for example. When a forming portion is provided only on one of the pair of rolls, a briquette having an asymmetric shape with only the upper side Bu (one of the sides) having a convex shape and its opposite surface having a planar shape, as illustrated in FIG. 6A to FIG. 6C. Thus, with a configuration of deciding the front and back of the briquette sample B, when the briquette having an asymmetric shape on the upper and lower sides as illustrated in FIG. 6A to FIG. 6C is inspected and the crush strength thereof is measured at the crush strength measuring unit 3, it is possible to set the attitude of the briquette sample B at a more appropriate one for measuring the crush strength. In such a case, preferably, the holder 9 further includes an inversion mechanism for inverting the front and back of the briquette sample B that the holder 9 holds. Additionally, a configuration having such an inversion mechanism can omit one of the pair of upper and lower laser measuring devices 12, so that the other of the pair of upper and lower laser measuring devices 12 can carryout the laser scanning for the volume of the briquette sample B.

Furthermore, in the above embodiment, for example, the description has been given of the case where the image processing unit 4 picks up images of the briquette sample B at the camera 15, and the data processing unit 5 calculates the project area of the briquette sample B based upon the image data and determines appropriateness or inappropriateness for the measurement target. However, the present invention is not limited to this. The volume measuring unit 2 can calculate the project area of the briquette sample B.

For example, the volume measuring unit 2 measures the outer shape of the briquette sample B by laser scanning, and the data processing unit 5 checks the outer shape data of the briquette sample B obtained by the volume measuring unit 2 with the predefined template. When the difference in the area between the outer shape data and the template exceeds a preset range of the area, the briquette sample B is determined to be inappropriate for the measurement target, so that such an inappropriate briquette sample B can be excluded from the measurement targets at the volume measuring unit 2 in accordance with the cross-sectional shape data and at the measurement targets at the crush strength measuring unit 3. Such a configuration can omit the image processing unit 4 including the camera 15.

Moreover, in the above embodiment, the briquetting machine has been described as an example of the granulator and the briquettes produced by the briquetting machine have been described as an example of the granulated substances. However, the application of the present invention is not limited to them. For example, the granulated substances can be substances named pellet or tablet, and in addition to the briquetting machine, any machine for rolling granulation, extrusion granulation, tableting, or the like is applicable.

REFERENCE SIGNS LIST 1 weight measuring unit
2 volume measuring unit
3 crush strength measuring unit
4 image processing unit
5 data processing unit
6 conveyance feeder
7 linear guide device
8 slide mechanism
9 holder
10 briquette inspection device
11 load cell
12 laser measuring device
13 pressing mechanism
14 disposal outlet
15 camera
16 opening and closing device
17 detection sensor
18 guide rail
20 housing
21 load cell
22 pressing unit
B briquette sample

The invention claimed is:
1. A briquette inspection device, comprising:
a conveyance feeder configured to receive a briquette sample;
a linear guide device configured to be arranged at a downstream side of the conveyance feeder, and to guide the briquette sample in a sliding direction;
a weight measuring unit configured to measure a weight of the briquette sample;
a volume measuring unit configured to measure a volume of the briquette sample by laser scanning; and
a crush strength measuring unit configured to measure a crush strength of the briquette sample by pressing the briquette sample after the volume measuring unit measures the volume of the briquette sample,
wherein the weight measuring unit, and the volume measuring unit, and the crush strength measuring unit are configured to be sequentially arranged from an upstream side of a conveyance direction of the briquette sample in the sliding direction of the linear guide device, and
wherein the weight, the volume, and the crush strength of the briquette sample are sequentially measured from the upstream side of the conveyance direction of the briquette sample in the sliding direction of the linear guide device.

2. The briquette inspection device according to claim 1, further comprising:
a data processing unit configured to process data of the volume measured by the volume measuring unit and data of the weight measured by the weight measuring unit,
wherein the data processing unit is configured to calculate an apparent density of the briquette sample from the volume measured by the volume measuring unit and the weight measured by the weight measuring unit.

3. The briquette inspection device according to claim 2,
wherein the volume measuring unit is configured to measure a cross-sectional shape of the briquette sample by a pair of upper and lower laser measuring devices carrying out laser scanning from above and below on the briquette sample, and
wherein the data processing unit is configured to distinguish a front and a back of the briquette sample based upon data of the cross-sectional shape measured by the volume measuring unit.

4. The briquette inspection device according to claim 3, further comprising an image processing unit configured to pick up an image of the briquette sample before the volume measuring unit measures the volume of the briquette sample and the crush strength measuring unit measures the crush strength of the briquette sample,
wherein the data processing unit is configured to check data of the image of the briquette sample picked up by the image processing unit with a predefined template, and when a difference in an area between the data of the image and the predefined template exceeds a preset range of the area, the data processing unit is configured to determine the briquette sample to be inappropriate for a measurement target and to exclude the briquette sample from the measurement target at the volume measuring unit and at the crush strength measuring unit.

5. The briquette inspection device according to claim 3,
wherein the volume measuring unit is configured to measure an outer shape of the briquette sample by the laser scanning, and
wherein the data processing unit is configured to check data of the outer shape of the briquette sample measured by the volume measuring unit with a predefined template, and when a difference in an area between the data of the outer shape and the predefined template exceeds a preset range of the area, the data processing unit is configured to determine the briquette sample to be inappropriate for a measurement target and to exclude the briquette sample from the measurement target based upon the cross-sectional shape at the volume measuring unit and at the crush strength measuring unit.

6. The briquette inspection device according to claim 2, further comprising an image processing unit configured to pick up an image of the briquette sample before the volume measuring unit measures the volume of the briquette sample and the crush strength measuring unit measures the crush strength of the briquette sample, wherein the data processing unit is configured to check data of the image of the briquette sample picked up by the image processing unit with a predefined template, and when a difference in an area between the data of the image and the predefined template exceeds a preset range of the area, the data processing unit is configured to determine the briquette sample to be inappropriate for a measurement target and to exclude the briquette sample from the measurement target at the volume measuring unit and at the crush strength measuring unit.

7. The briquette inspection device according to claim 2, wherein the volume measuring unit is configured to measure an outer shape of the briquette sample by the laser scanning, and wherein the data processing unit is configured to check data of the outer shape of the briquette sample measured by the volume measuring unit with a predefined template, and when a difference in an area between the data of the outer shape and the predefined template exceeds a preset range of the area, the data processing unit is configured to determine the briquette sample to be inappropriate for a measurement target and to exclude the briquette sample from the measurement target based upon the cross-sectional shape at the volume measuring unit and at the crush strength measuring unit.

8. A briquette inspection method, comprising:

receiving a briquette sample by a conveyance feeder;

feeding the briquette sample to a linear guide device arranged at a downstream side of the conveyance feeder to guide the briquette sample in a sliding direction;

measuring a weight of the briquette sample;

measuring a volume of the briquette sample by laser scanning; and measuring a crush strength of the briquette sample by pressing the briquette sample after the measuring step measures the volume of the briquette sample, wherein the step of measuring the weight of the briquette sample, the step of measuring the volume of the briquette sample, and the step of measuring the crush strength of the briquette sample are sequentially performed from an upstream side of a conveyance direction of the briquette sample in the sliding direction of the linear guide device.

\* \* \* \* \*